United States Patent
Kim et al.

(10) Patent No.: US 11,246,477 B2
(45) Date of Patent: Feb. 15, 2022

(54) FLUORESCENCE ENDOSCOPIC METHOD FOR VISUALIZATION OF COLORECTAL TISSUE USING FLUOROQUINOLONE ANTIBIOTICS AND METHOD FOR DIAGNOSIS OF LESIONS OF COLORECTAL TISSUE USING

(71) Applicants: POSTECH ACADEMY-INDUSTRY FOUNDATION, Pohang-si (KR); THE ASAN FOUNDATION, Seoul (KR); UNIVERSITY OF ULSAN FOUNDATION FOR INDUSTRY COOPERATION, Ulsan (KR); OSONG MEDICAL INNOVATION FOUNDATION, Cheongju-si (KR)

(72) Inventors: Seong Han Kim, Seoul (KR); Seunghun Lee, Daegu (KR); Hoon Cheol Jang, Seoul (KR); Bumju Kim, Pohang-si (KR); Viet Hoan Le, Pohang-si (KR); Wonyeong Park, Busan (KR); Ki Hean Kim, Pohang-si (KR); Seung Jae Myung, Seoul (KR); Seungrag Lee, Cheongju-si (KR)

(73) Assignees: POSTECH ACADEMY-INDUSTRY FOUNDATION, Pohang-si (KR); THE ASAN FOUNDATION, Seoul (KR); UNIVERSITY OF ULSAN FOUNDATION FOR INDUSTRY COOPERATION, Ulsan (KR); OSONG MEDICAL INNOVATION FOUNDATION, Cheongju-si (KR)

( * ) Notice: Subject to any disclaimer, the term of this patent is extended or adjusted under 35 U.S.C. 154(b) by 251 days.

(21) Appl. No.: 16/289,555

(22) Filed: Feb. 28, 2019

(65) Prior Publication Data
US 2020/0275829 A1  Sep. 3, 2020

(51) Int. Cl.
*A61B 1/04*  (2006.01)
*A61B 5/00*  (2006.01)
*A61K 31/496*  (2006.01)

(52) U.S. Cl.
CPC .............. *A61B 1/043* (2013.01); *A61B 1/042* (2013.01); *A61B 5/0071* (2013.01); *A61B 5/0084* (2013.01); *A61K 31/496* (2013.01)

(58) Field of Classification Search
CPC ........... A61B 1/043; A61B 1/042; A61B 1/31; A61B 1/0638; A61B 5/0084; A61B 5/0071; A61B 5/4255; A61K 31/496
See application file for complete search history.

(56) References Cited

U.S. PATENT DOCUMENTS

2016/0341734 A1\* 11/2016 Kim .................. G01N 21/6428
2017/0325790 A1\* 11/2017 Blitzer .............. A61M 25/1002
(Continued)

OTHER PUBLICATIONS

Xiong et al,. "Investigation on the interaction of antibacterial drug moxifloxacin hydrochloride with human serum albumin using multi-spectroscopic approaches, molecular docking and dynamical simulation" RSC Adv., 2017, 7, 48942 (Year: 2017).\*
(Continued)

*Primary Examiner* — Colin T. Sakamoto
(74) *Attorney, Agent, or Firm* — Revolution IP, PLLC (57) ABSTRACT

A fluorescence endoscopic method for visualization of colorectal tissue using a fluoroquinolone antibiotic and a method for diagnosis of lesions of colorectal tissue using the same. The fluorescence endoscopic method for visualization of colorectal tissue includes staining goblet cells of the colorectal tissue with moxifloxacin, which is a fluoroquinolone antibiotic, and exciting the stained goblet cells with single photons in the near UV region or in the visible region, followed by fluorescence endoscopic photographing of the goblet cells, thereby enabling acquisition of morphological information on living tissue without damage to or destruction of the colorectal tissue, while allowing diagnosis of lesions of the colon based on the morphological information on living tissue such as information on the distribution of the goblet cells. Specifically, the fluorescence endoscopic method includes: a colorectal tissue staining step in which the crypt of the colorectal tissue is stained with a fluoroquinolone antibiotic; an image pickup unit insertion step in which an image pickup unit is inserted into the colon; a light irradiation step in which the colorectal tissue is irradiated
(Continued)

with excitation light from a light source of the image pickup unit; a colorectal tissue photographing step in which the colorectal tissue is photographed using a photographing device of the image pickup unit through the fluoroquinolone antibiotic fluorescence-excited by light in the light irradiation step, wherein, in the colorectal tissue staining step, goblet cells of the crypt are stained with the fluoroquinolone antibiotic; in the light irradiation step, the light source emits single photons as excitation light inducing fluorescence of the fluoroquinolone antibiotic, the excitation light from the light source having a wavelength band within the near UV and visible regions; and, in the image pickup unit insertion step, the image pickup unit is a general fluorescence endoscope or a confocal endoscopic microscope.

9 Claims, 7 Drawing Sheets

(56) References Cited

U.S. PATENT DOCUMENTS

| | | | |
|---|---|---|---|
| 2019/0033326 A1* | 1/2019 | Liu | A61K 31/4245 |
| 2019/0059737 A1* | 2/2019 | Lee | A61B 1/0638 |

OTHER PUBLICATIONS

Stone et al., "Fluorescent Antibiotics: New Research Tools to Fight Antibiotic Resistance" Trends in Biotechnology, May 2018, vol. 36, No. 5 (Year: 2018).*

Lee et al., "In vivo 3D measurement of moxifloxacin and gatifloxacin distributions in the mouse ornea using multiphoton microscopy" Scientific Reports | 6:25339 2016 (Year: 2016).*

Wang et al., "Moxifloxacin: Clinically compatible contrast agent for multiphoton imaging" Scientific Reports | 6:27142, 2016 (Year: 2016).*

Gersemann et al., "Differences in goblet cell differentiation between Crohn's disease and ulcerative colitis" Differentiation 77 (2009) 84-94 (Year: 2009).*

Lee, "Background Mucosal Changes in Colorectal Carcinomas" Cancer, vol. 61, Apr. 15, 1988, pp. 1563-1570 (Year: 1988).*

Parikh et al., "Confocal laser endomicroscopy features of sessile serrated adenomas/polyps" United European Gastroenterology Journal, 2016, vol. 4(4) 599-603 (Year: 2016).*

* cited by examiner

FLUORESCENCE ENDOSCOPIC METHOD FOR VISUALIZATION OF COLORECTAL TISSUE USING FLUOROQUINOLONE ANTIBIOTICS AND METHOD FOR DIAGNOSIS OF LESIONS OF COLORECTAL TISSUE USING

STATEMENT REGARDING RESEARCH

The research related to this disclosure was supported by the projects listed below:
[Project number] 1415157444
[Ministry] Ministry of Trade, Industry and Energy
[Management agency] Korea Evaluation Institute of Industrial Technology
[Program name] Industrial Technology Innovation Program (10063408) by the Ministry of Trade, Industry & Energe (MOTIE, Korea)
[Project name] Development of channel-inserted convergence smart endoscopic system based on multispectral fluorescence imaging for precise diagnosis of digestive diseases
[Contribution ratio] 20%
[Supervision institution] Asan Medical Center
[Period] Jan. 1, 2018~Dec. 31, 2018
[Project number] 1711068372
[Ministry] Ministry of Science and ICT
[Management Agency] National Research Foundation of Korea
[Program name] Korea-Sweden Research Cooperation Program (2017R1A2A1A18070960) of the National Research Foundation (NRF) funded by the Korean Government (MEST)
[Project name] In vivo screening of apatamers for diabetes treatment
[Contribution ratio] 40%
[Supervision institution] POSTECH Research and Business Development Foundation
[Period] Mar. 1, 2018~Feb. 28, 2019
[Project number] 1711070054
[Ministry] Ministry of Science and ICT
[Management Agency] National Research Foundation of Korea
[Program name] The Brain Research Program through the National Research Foundation of Korea(NRF) funded by the Ministry of Science, ICT & Future Planning (NRF-2017M3C7A 1044964)
[Project name] Development of high-speed 3D fluorescence microscope systems for comprehensive molecular imaging of optical cleared mouse brains
[Contribution ratio] 40%
[Supervision institution] POSTECH Research and Business Development Foundation
[Period] Mar. 1, 2018~Dec. 31, 2018

FIELD

The present invention relates to a fluorescence endoscopic method for visualization of colorectal tissue using fluoroquinolone antibiotics and a method for diagnosis of lesions of colorectal tissue using the same. More particularly, the present invention relates to a fluorescence endoscopic method for visualization of colorectal tissue, which includes staining goblet cells of colorectal tissue using moxifloxacin as a fluoroquinolone antibiotic and exciting the stained goblet cells with single photons in the near UV region or in the visible region, followed by fluorescence endoscopic photographing of the goblet cells, thereby enabling acquisition of morphological information on living tissue without damage to or destruction of the colorectal tissue, while allowing diagnosis of lesions of the colon based on the morphological information on living tissue such as information on the distribution of the goblet cells.

BACKGROUND

Optical microscopy capable of high-resolution photographing of cells in living tissue is used in biological research and for clinical diagnosis in ophthalmology and dermatology.

In clinical diagnosis, non-invasive optical microscopy, which mainly utilizes reflection of light, is used, and an example of the non-invasive optical microscopy includes confocal reflectance microscopy.

However, an image of cells of living tissue obtained by confocal reflectance microscopy has low contrast. Accordingly, when there is a need for enhancement of image contrast, fluorescence microscopy, in which living tissue is stained with a fluorescent material (a fluorescent probe), followed by excitation fluorescence photographing of the living tissue, is used.

Here, the fluorescent material allows emission of strong fluorescence signals from a specific region of interest, thereby enabling high-contrast and high-speed imaging.

Although various fluorescent materials are used for animal subjects, indocyanine green, fluorescein and the like are used for the human body as a fluorescent material for staining of blood vessels.

Since staining of blood vessels alone is not enough to diagnose lesions or cancer, or to obtain morphological information on cells, staining of cells in the human body is necessary for accurate diagnosis.

For this purpose, although various studies have been made to develop fluorescent medicines for staining of human cells, a fluorescent material applicable to the human body has not been developed in the art due to toxicity to cells and the like.

Among non-toxic medicines that can be used to stain human cells, moxifloxacin is an antibacterial agent used to treat or prevent bacterial infections in clinical practice and has properties suitable for staining of living tissue and fluorescence imaging, such as intrinsic fluorescence and high penetrability to living tissue.

However, since excitation efficiency of moxifloxacin reaches maximum at 280 nm in the mid-UV region, which is harmful to the human body, it is difficult to use moxifloxacin in in-vivo photographing of the human body.

In order to resolve such a problem, recently, fluorescence imaging based on two-photon excitation of moxifloxacin at a near-infrared excitation wavelength has been demonstrated and it was confirmed that human tissue and cells can be stained with moxifloxacin, thereby enabling acquisition of a high resolution image thereof.

In western countries, 5% or more of the population suffers from colon cancer, and adults over the age of 54 are more likely to develop colon cancer than any other ages. It is known that rates of colon cancer can be greatly reduced by detecting and resecting colorectal polyps and tumors through regular colonoscopy screenings.

However, despite the usefulness of colonoscopy, an examination using a conventional white-light endoscope has a relatively high rate of missing adenomas, causing the risk of overlooking colorectal lesions.

Particularly, a flat adenoma very slightly differs in color from normal colon mucosal tissue and has either a completely flat shape or a slightly depressed shape, such that even experienced endoscopy specialists have difficulty in detection of the flat adenoma through conventional colonoscopy screenings.

Recently, specialized endoscopic techniques have been developed to increase the contrast of endoscopic images to achieve more efficient detection of small flat colorectal lesions.

Examples of the specialized endoscopic techniques include: chromoendoscopy, in which a cell staining solution such as methylene blue is sprayed onto target cells, followed by endoscopic photographing of the cells; narrow-band imaging (NBI), which uses an illumination light source emitting light having a wavelength band that can be selectively absorbed by colorectal tissue instead of a white light source to increase imaging contrast; autofluorescence endoscopy, in which photographing of colorectal tissue is conducted by detecting autofluorescence from the colorectal tissue; and confocal laser scanning endomicroscopy (CLE), in which a fluorescent cell dye is sprayed into target cells, followed by cell-level photographing, thereby allowing non-invasive biopsy of abnormal lesions.

Thereamong, chromoendoscopy has a drawback in that a residual solution needs to be washed out after spraying of methylene blue, and confocal laser scanning endomicroscopy (CLE) has a problem in that clinically approved fluorescent cell dyes are limited.

PRIOR LITERATURE (Patent document 0001) Korean Patent Publication No. 10-2016-0136738 (Title of the Invention: USE OF FLUOROQUINOLONE ANTIBIOTICS, Publication date: Nov. 30, 2016)

SUMMARY

It is an aspect of the present invention to provide a method for diagnosis of lesions of colorectal tissue using the same, and, more particularly, to a fluorescence endoscopic method for visualization of colorectal tissue, which includes staining goblet cells of colorectal tissue using moxifloxacin as a fluoroquinolone antibiotic and exciting the stained goblet cells with single photons in the near UV region or in the visible region, followed by fluorescence endoscopic photographing of the goblet cells, thereby enabling acquisition of morphological information on living tissue without damage to or destruction of the colorectal tissue, while allowing diagnosis of lesions of the colon based on the morphological information on living tissue such as information on the distribution of the goblet cells.

In accordance with one aspect of the present invention, there is provided a fluorescence endoscopic method for visualization of colorectal tissue using a fluoroquinolone antibiotic, including: a colorectal tissue staining step in which the crypt of the colorectal tissue is stained with a fluoroquinolone antibiotic; an image pickup unit insertion step in which an image pickup unit is inserted into the colon; a light irradiation step in which the colorectal tissue is irradiated with excitation light from a light source of the image pickup unit; a colorectal tissue photographing step in which the colorectal tissue is photographed using a photographing device of the image pickup unit through the fluoroquinolone antibiotic fluorescence-excited by light in the light irradiation step, wherein, in the colorectal tissue staining step, goblet cells of the crypt are stained with the fluoroquinolone antibiotic; in the light irradiation step, the light source emits single photons as excitation light inducing fluorescence of the fluoroquinolone antibiotic, the excitation light from the light source having a wavelength band within the near UV and visible regions; and in the image pickup unit insertion step, the image pickup unit is a general fluorescence endoscope or a confocal endoscopic microscope.

In the colorectal tissue staining step, the fluoroquinolone antibiotic used to stain the colorectal tissue may include moxifloxacin.

In the light irradiation step, the wavelength band within the near UV and visible regions may range from 300 nm to 476 nm.

In accordance with another aspect of the present invention, there is provided a method for diagnosis of lesions of colorectal tissue using an image of goblet cells of the colorectal tissue obtained by the fluorescence endoscopic method for visualization of colorectal tissue set forth above, wherein diagnosis of the lesions of the colorectal tissue is conducted based on change in the number of goblet cells per unit area.

The lesions of the colorectal tissue may include ulcerative colitis, Crohn's disease, hyperplasia, and adenoma.

The fluorescence endoscopic method for visualization of colorectal tissue using fluoroquinolone antibiotics and the method for diagnosis of lesions of colorectal tissue have the following effects:

First, since the colorectal tissue is stained with moxifloxacin, followed by irradiation of moxifloxacin with light in the visible region, high-speed direct photographing of the structure of the crypt is possible without damage to the colorectal tissue, thereby allowing quick and accurate diagnosis.

Second, since goblet cells of the colorectal tissue are stained with moxifloxacin to exhibit higher fluorescence intensity than surrounding cells, such that the crypt can be distinct, the crypt can be easily photographed even using a general fluorescence endoscope, which cannot provide 3D images.

Third, lesions of the colorectal tissue can be diagnosed based on numerical or morphological changes of goblet cells of the colorectal tissue.

DRAWINGS

FIG. 4(a), FIG. 4(a1) and FIG. 4(b) are images of extracted and moxifloxacin-stained colorectal tissue of a mouse, obtained by the fluorescent imaging method for visualization of colorectal tissue using fluoroquinolone antibiotics according to the present invention.

FIG. 5(a), FIG. 5(a1), FIG. 5(b), and FIG. 5(b1) are images of moxifloxacin-stained colorectal tissue of a living mouse, obtained by the the fluorescent imaging method or visualization of colorectal tissue using fluoroquinolone antibiotics according to the present invention.

FIG. 6(a), FIG. 6(a1), FIG. 6(b), and FIG. 6(b1) are images of moxifloxacin-stained colorectal tissue of a living mouse ingesting dextran sodium sulfate (DSS), obtained by the fluorescent imaging method for visualization of colorectal tissue using fluoroquinolone antibiotics according to the present invention.

FIG. 7(a1), FIG. 7(a2), FIG. 7(b1), and FIG. 7(b2) are endoscopy images of moxifloxacin-stained colorectal tissue of a living mouse, obtained by the fluorescence endoscopic method for visualization of colorectal tissue using fluoroquinolone antibiotics. FIG. 7(a1) and FIG. 7(a2) are confocal endoscopic microscope images of the moxifloxacin-stained colorectal tissue of a normal mouse, and FIG. 7(b1) and FIG. 7(b2) are confocal endoscopic microscope images of the moxifloxacin-stained colorectal tissue of the mouse ingesting DDS.

DETAILED DESCRIPTION

Hereinafter, embodiments of the present invention will be described with reference to the accompanying drawings. It should be noted that like components will be denoted by like reference numerals throughout the specification and the accompanying drawings. In addition, descriptions of details apparent to those skilled in the art will be omitted for clarity.

Now, a fluorescence endoscopic method for visualization of colorectal tissue using fluoroquinolone antibiotics according to the present invention will be described with reference to FIG. 1 to FIG. 7(b2).

Figure 1:
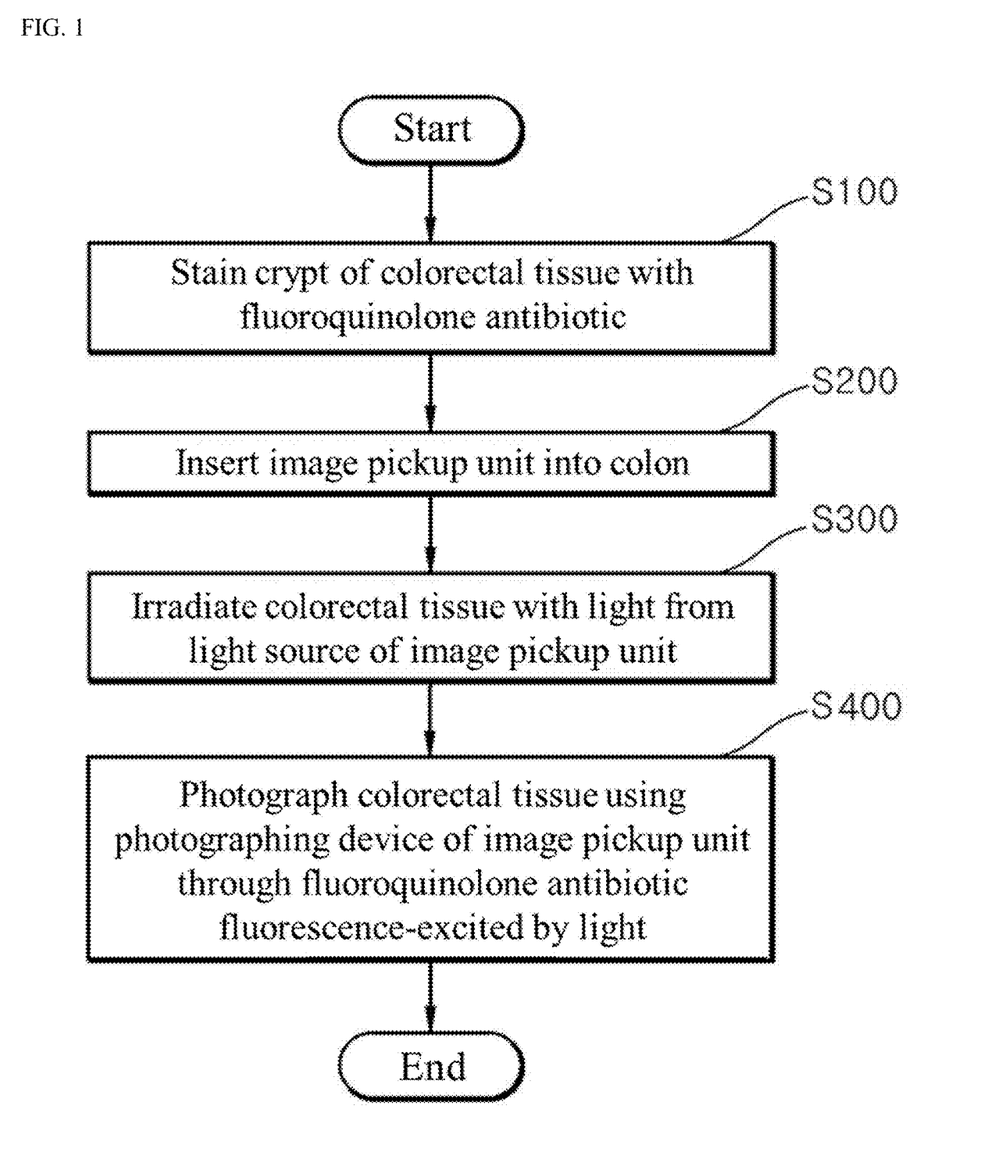
FIG. 1 is a flow diagram of a fluorescence endoscopic method for visualization of colorectal tissue using fluoroquinolone antibiotics.

Referring to FIG. 1, the fluorescence endoscopic method for visualization of colorectal tissue using fluoroquinolone antibiotics according to the present invention includes a colorectal tissue staining step staining step S100, an image pickup unit insertion step S200, a light irradiation step S300, and a colorectal tissue photographing step S400.

Prior to describing the fluorescence endoscopic method according to the present invention, a mechanism of single-photon excitation will be described with reference to FIG. 2.

Figure 2:
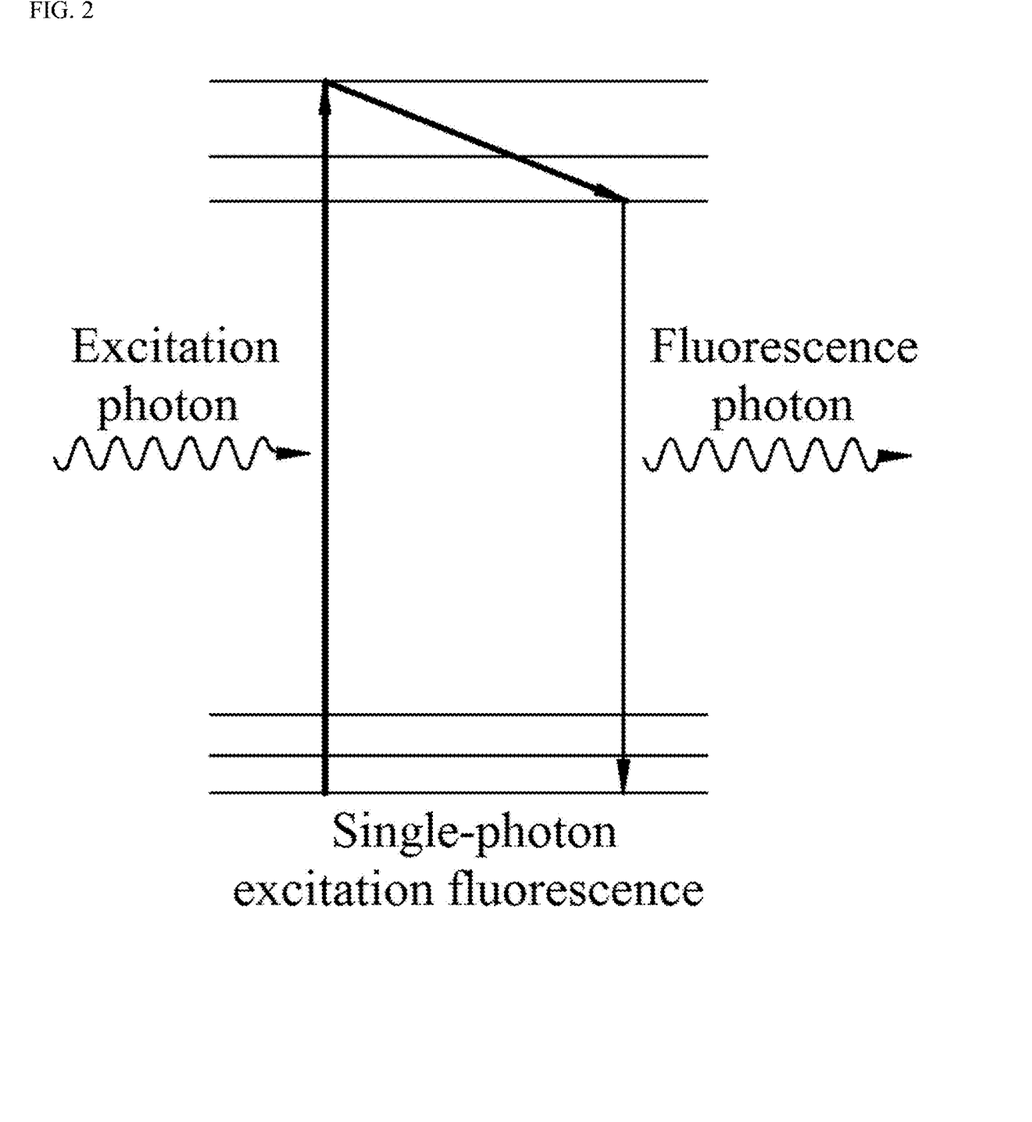
FIG. 2 is a diagram illustrating a mechanism of single-photon excitation used in the fluorescence endoscopic method for visualization of colorectal tissue using fluoroquinolone antibiotics.

Referring to FIG. 2, the energy level of an electron in a molecule of a fluorescent material is raised to an excited state from a ground state by an excitation photon.

Then, the electron relaxes to the ground state by emitting a fluorescence photon. Here, the electron absorbs one excitation photon and emits one fluorescence photon, a phenomenon called single-photon excitation fluorescence. Due to single-photon excitation fluorescence, single-photon excitation efficiency is higher than two-photon excitation efficiency, whereby fluorescence imaging is possible even when the luminous intensity of a light source described below is reduced.

That is, molecular activities in living cells or tissue can be observed at high resolution by optical fluorescence microscopy by treating the cells or tissue with a fluorescent material. This is because an electron in the fluorescent material emits a fluorescence photon having a unique color in the process of being excited by an excitation photon and returning to the original state thereof.

When such a fluorescent material is injected into living tissue and is absorbed by cells of the living tissue to be maintained at a high concentration, high-contrast photographing of the living tissue is possible through fluorescence of the fluorescent material.

That is, morphological information on living tissue can be obtained through staining of the living tissue with a fluorescent material, provided that the fluorescent material is not toxic to the human body and can be fluorescence-excited by light in the visible region, which is harmless to the human body.

Examples of the fluoroquinolone antibiotics used to stain living tissue may include moxifloxacin, gatifloxacin, pefloxacin, difloxacin, nofloxacin, ciprofloxacin, ofloxacin, and enrofloxacin. Herein, moxifloxacin capable of exhibiting autofluorescence in the visible region is used to stain living tissue.

Next, a single-photon excitation spectrum and fluorescence emission spectrum in the near UV and visible regions of moxifloxacin used in the fluorescence endoscopic method for visualization of colorectal tissue using fluoroquinolone antibiotics according to the present invention will be described with reference to FIG. 3(a) and FIG. 3(b).

Figure 3A:
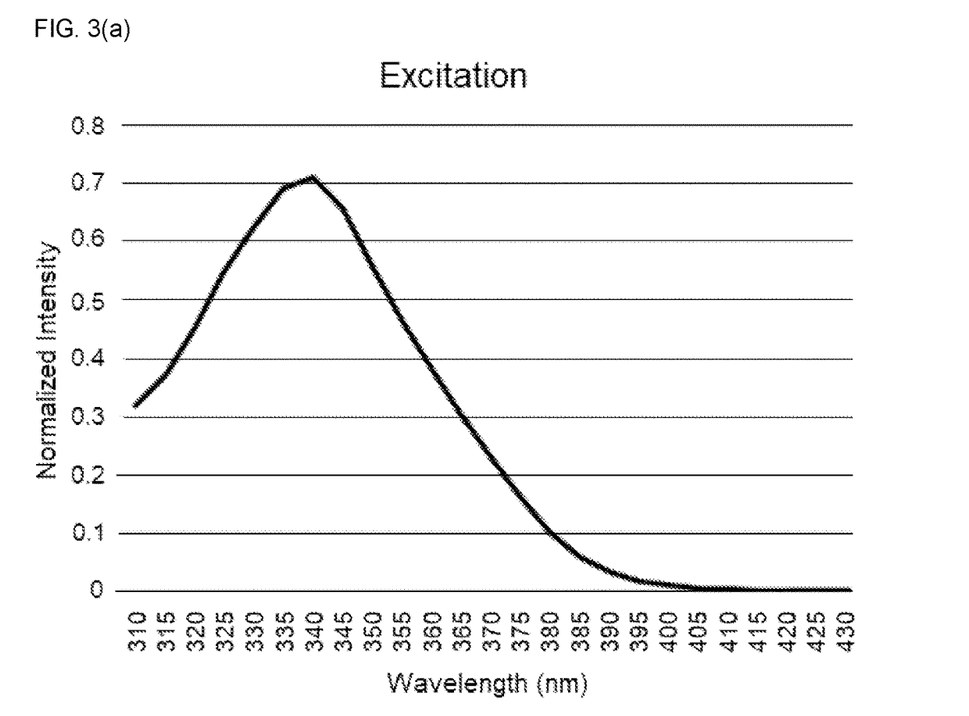
FIG. 3(a) and FIG. 3(b) show a single-photon excitation spectrum and fluorescence emission spectrum in the near UV region and visible regions of moxifloxacin used in the fluorescence endoscopic method for visualization of colorectal tissue using fluoroquinolone antibiotics.
Figure 3B:
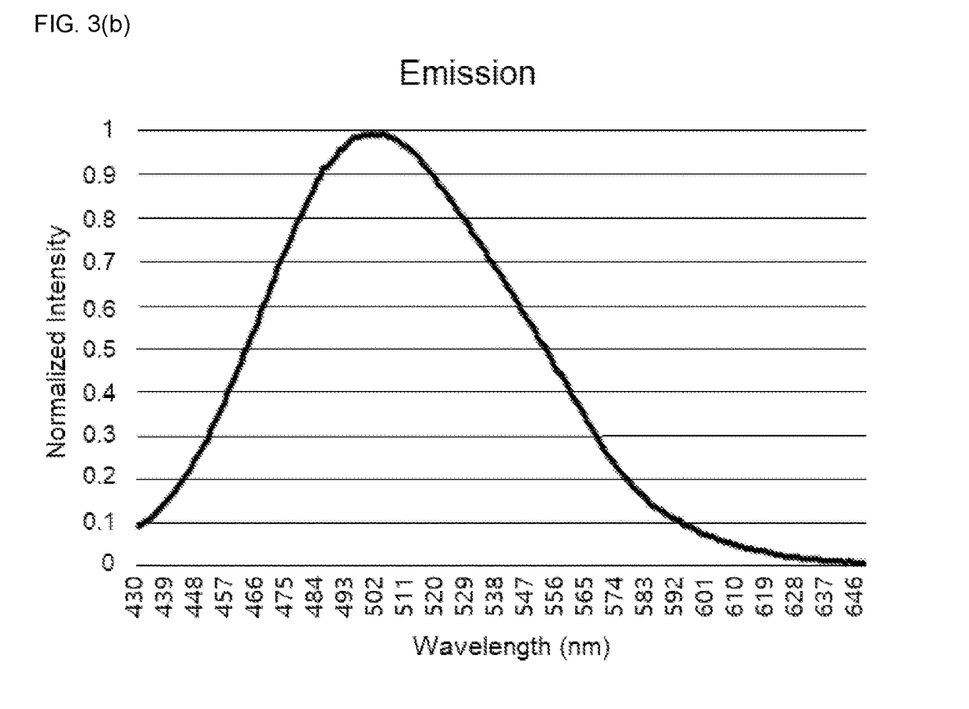

FIG. 3(a) and FIG. 3(b) show an excitation spectrum and fluorescence emission spectrum in the near UV and visible regions of moxifloxacin, respectively.

As moxifloxacin used in the fluorescence endoscopic method for visualization of colorectal tissue using fluoroquinolone antibiotics according to the present invention, Vigamox eye drop 0.5% commercially available from Alcon Lab Inc. (USA) was used.

As shown in FIG. 3(a) and FIG. 3(b), excitation efficiency of moxifloxacin had a maximum value at around 340 nm in the near UV region and then gradually decreased with increasing wavelength.

However, it was confirmed that excitation of moxifloxacin was also possible at a wavelength of 405 nm to 478 nm, which falls within the visible region outside the near UV region. Particularly, the fluorescence intensity at 405 nm was about 0.5% of that at 340 nm and was much higher than two-photon fluorescence intensity based on 700 nm excitation light.

Accordingly, in the fluorescence endoscopic method for visualization of colorectal tissue using fluoroquinolone antibiotics according to the present invention, an excitation light source emitting light in a wavelength band of 300 nm to 476 nm is used, such that imaging speed can be improved by increasing the intensity of fluorescence signals using light in the mid- to near-UV regions, while applicability to living tissue can be improved using light in the visible region.

In the aforementioned single-photon wavelength band, wavelengths falling within the near UV region can cause damage to cells of living tissue. However, based on the fact that single-photon excitation efficiency is high, these wavelengths can also be used for photographing of living tissue by reducing luminous intensity of the light source.

Next, the fluorescence endoscopic method for visualization of colorectal tissue using fluoroquinolone antibiotics according to the present invention will be described in detail with reference to FIG. 1.

In the colorectal tissue staining step S100, crypt of colorectal tissue, living tissue to be tested, is stained with a fluoroquinolone antibiotic. Herein, as the fluoroquinolone antibiotic, moxifloxacin, which is a fluoroquinolone antibiotic, is used.

In the conjunctiva staining step S100, goblet cells constituting the crypt of the colorectal tissue are stained with moxifloxacin.

In the image pickup unit insertion step S200, an image pickup unit is inserted into the colon for photographing of the colorectal tissue, wherein the image pickup unit includes a general fluorescence endoscope or a confocal endoscopic microscope.

In the light irradiation step S300, the colorectal tissue is irradiated with excitation light from a light source included in the image pickup unit. Here, the light source emits single photons, specifically excitation light having the aforementioned wavelength band in the near UV and visible ranges. In experimental examples described below, the light source emits continuous wave light having the aforementioned wavelength band in the near UV and visible regions to perform fluorescence excitation.

In the colorectal tissue photographing step S400, photographing of the goblet cells constituting the crypt of the colorectal tissue is conducted using a photographing device included in the image pickup unit through the fluoroquinolone antibiotic fluorescence-excited by light in the light irradiation step S300. Here, the photographed area of the colorectal tissue may include all regions of the colorectal tissue, from the cecum to the rectum.

Next, the fluorescence endoscopic method for visualization of colorectal tissue using fluoroquinolone antibiotics according to the present invention will be described in more detail with reference to experimental examples.

Figure 4:
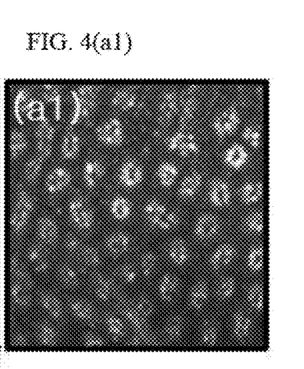
FIG. 4(a) is a confocal fluorescence microscopy image of the moxifloxacin-stained colorectal tissue of the mouse, FIG. 4(a1) is an enlarged (high-magnification) image of a part of FIG. 4(a)
FIG. 4(b) is a high-magnification fluorescence microscopy image of the moxifloxacin-stained colorectal tissue of the mouse.

Experimental Example 1: Photographing of Extracted and Moxifloxacin-Stained Colorectal Tissue of Mouse FIG. 4(a), FIG. 4(a1) and FIG. 4(b) are images of extracted and moxifloxacin-stained colorectal tissue of a mouse, obtained by the fluorescence endoscopic method for visualization of colorectal tissue using fluoroquinolone antibiotics according to the present invention.

Figure 4A:
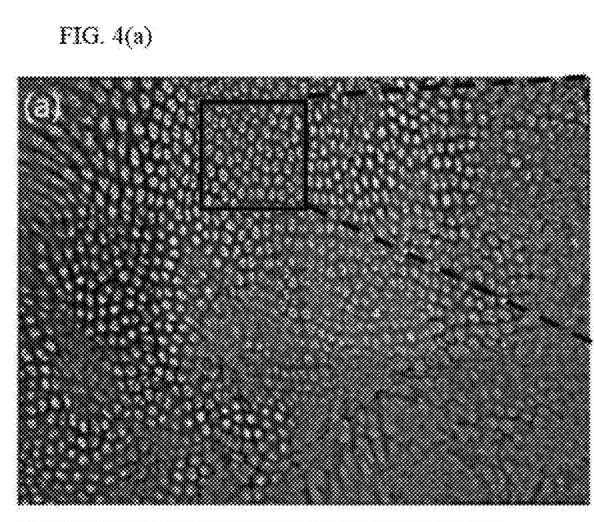

FIG. 4(a) and FIG. 4(a1) are confocal fluorescence microscopy images of the moxifloxacin-stained colorectal tissue of the mouse. Referring to FIG. 4(a) and FIG. 4(a1), goblet cells of the colorectal tissue stained with moxifloxacin were fluorescence-excited and emitted light, whereby the crypt and goblet cells of the colorectal tissue could be observed.

Figure 4B:
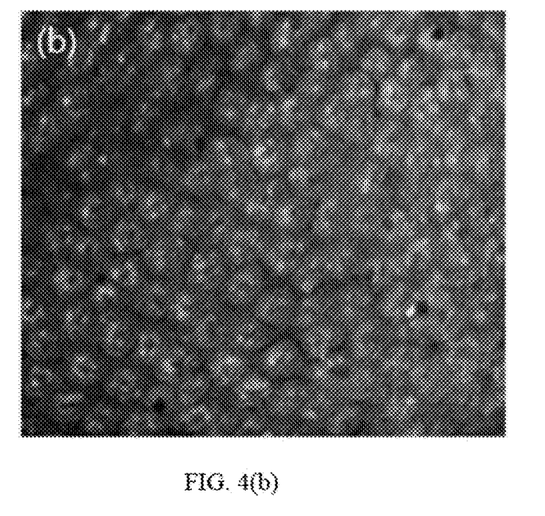

FIG. 4(b) is a high-magnification fluorescence microscopy image of the moxifloxacin-stained colorectal tissue of the mouse. Referring to FIG. 4(b), goblet cells of the colorectal tissue stained with moxifloxacin were fluorescence-excited and emitted light, whereby the crypt and goblet cells of the colorectal tissue could be observed.

Therefore, it was confirmed that, through staining of goblet cells of extracted colorectal tissue of a mouse with moxifloxacin, high-resolution imaging of the goblet cells is possible even using a high-magnification fluorescence microscope instead of a high-performance microscope such as a confocal fluorescence microscope.

Experimental Example 2: Photographing of Moxifloxacin-Stained Colorectal Tissue of Living Mouse FIG. 5(a), FIG. 5(a1), FIG. 5(b), and FIG. 5(b1) are images of moxifloxacin-stained colorectal tissue of a living mouse, obtained by the fluorescence endoscopic method for visualization of colorectal tissue using fluoroquinolone antibiotics according to the present invention.

Figures 5, 5A:
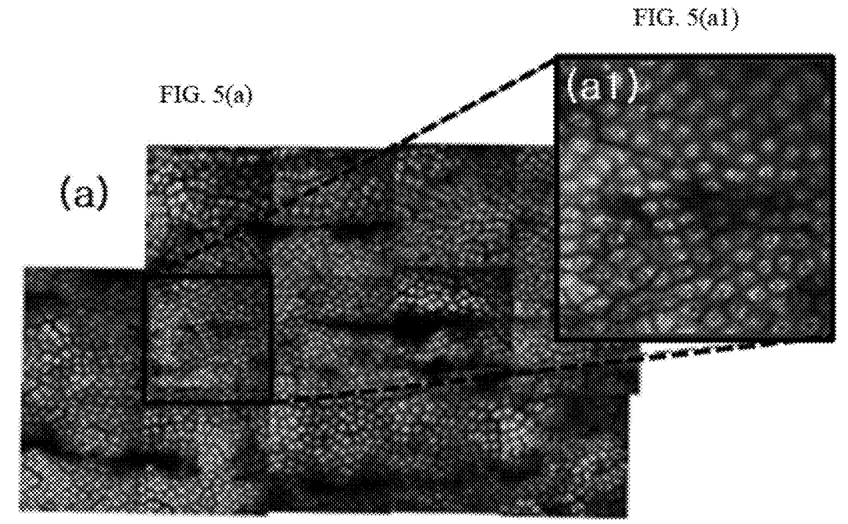
FIG. 5(a) is a confocal fluorescence microscopy image of the moxifloxacin-stained colorectal tissue of the mouse, FIG. 5(a1) is an enlarged (high-magnification) image of a part of FIG. 5(a)

FIG. 5(a) is a confocal fluorescence microscopy image of the moxifloxacin-stained colorectal tissue of the mouse and FIG. 5(a1) is an enlarged (high-magnification) image of a part of FIG. 5(a). Referring to FIG. 5(a) and FIG. 5(a1), goblet cells of the colorectal tissue stained with moxifloxacin was fluorescence-excited and emitted light, whereby the crypt and goblet cells of the colorectal tissue could be observed.

Figures 5, 5B:
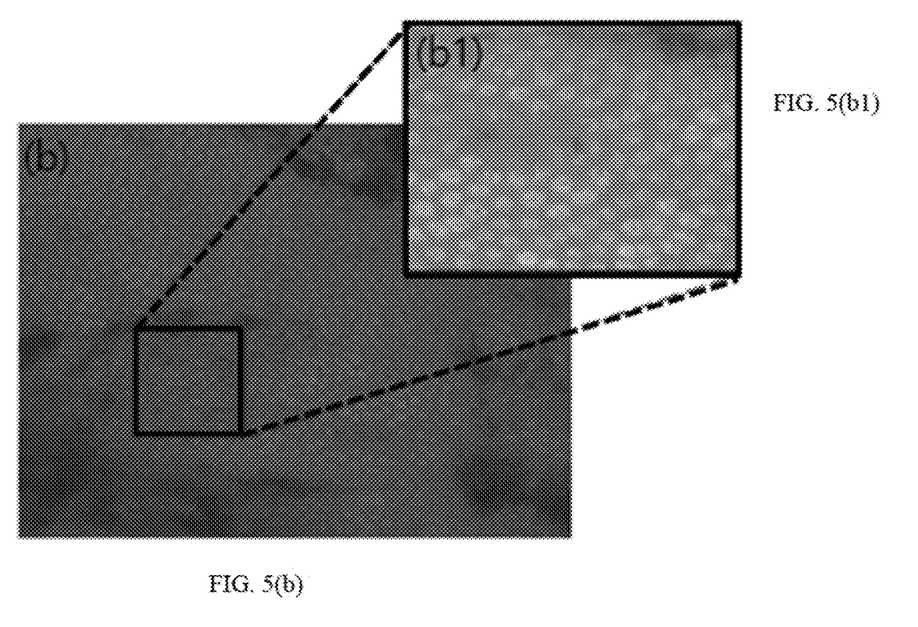
FIG. 5(b) is a high-magnification fluorescence microscopy image of the moxifloxacin-stained colorectal tissue of the mouse, and FIG. 5(b1) is an enlarged (high-magnification) image of a part of FIG. 5(b).

FIG. 5(b) is a high-magnification fluorescence microscopy image of the moxifloxacin-stained colorectal tissue of the mouse and FIG. 5(b1) is an enlarged (high-magnification) image of a part of FIG. 5(b). Referring to FIG. 5(b) and FIG. 5(b1), goblet cells of the colorectal tissue stained with moxifloxacin were fluorescence-excited and emitted light, whereby the crypt and goblet cells of the colorectal tissue could be observed.

Therefore, it was confirmed that, through staining of goblet cells of colorectal tissue of a living mouse with moxifloxacin, high-resolution imaging of the goblet cells is possible even using a high-magnification fluorescence microscope instead of a high-performance microscope such as a confocal fluorescence microscope, while photographing of living tissue can be conducted without damage to the living tissue.

Experimental Example 3: Photographing of Moxifloxacin-Stained Colorectal Tissue of Living Mouse Ingesting DSS FIG. 6(a), FIG. 6(a1), FIG. 6(b), and FIG. 6(b1) are images of moxifloxacin-stained colorectal tissue of a mouse ingesting dextran sodium sulfate (DSS), obtained by the fluorescence endoscopic method for visualization of colorectal tissue using fluoroquinolone antibiotics according to the present invention.

Figures 6, 6B:
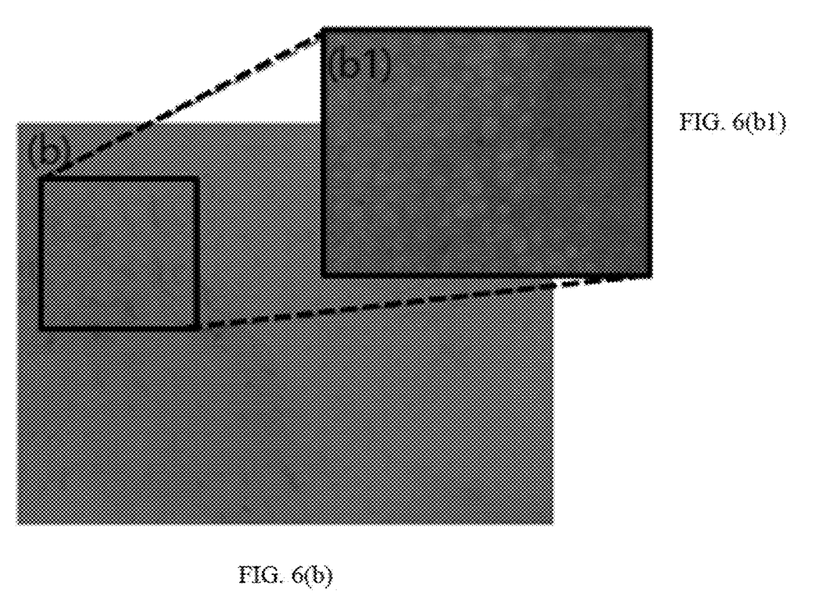
FIG. 6(b) is a high-magnification fluorescence microscopy image of the moxifloxacin-stained colorectal tissue of the mouse, and FIG. 6(b1) is an enlarged (high-magnification) image of a part of FIG. 6(b).
Figures 6, 6A:
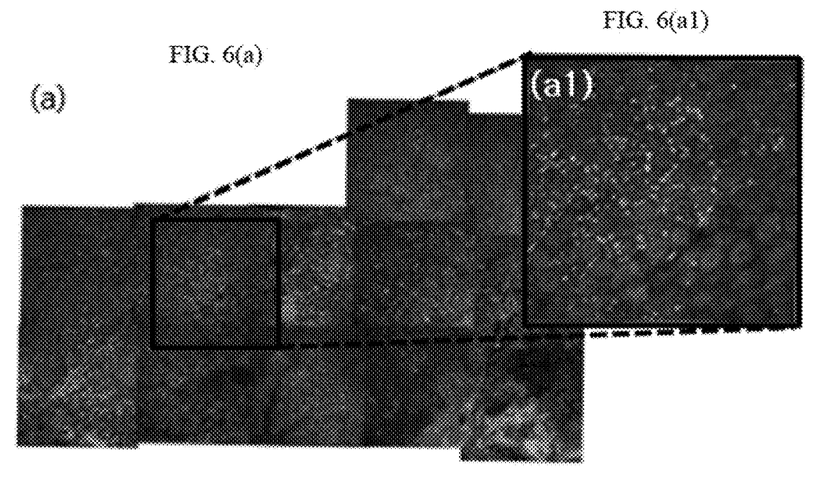
FIG. 6(a) is a confocal fluorescence microscopy image of the moxifloxacin-stained colorectal tissue of the mouse, FIG. 6(al) is an enlarged (high-magnification) image of a part of FIG. 6(a)

FIG. 6(a) is a confocal fluorescence microscopy image of the moxifloxacin-stained colorectal tissue of the mouse and FIG. 6(a1) is an enlarged (high-magnification) image of a part of FIG. 6(a). Referring to FIG. 6(a) and FIG. 6(a1), it could be observed that, in the colorectal tissue of the mouse ingesting DSS, there was no light emission from cells due to collapse of the crypt or destruction of the goblet cells caused by DSS.

FIG. 6(b) is a high-magnification fluorescence microscopy image of the moxifloxacin-stained colorectal tissue of the mouse and FIG. 6(b1) is an enlarged (high-magnification) image of a part of FIG. 6(b). Referring to FIGS. 6(b) and 6(b1), it could be observed that, in the colorectal tissue of the mouse ingesting DSS, there was no light emission from cells due to collapse of the crypt or destruction of the goblet cells caused by DSS.

Therefore, it was confirmed that, through staining of goblet cells of colorectal tissue of a mouse with moxifloxacin, high-resolution imaging of the goblet cells is possible using a high-magnification fluorescence microscope instead of a high-performance microscope such as a confocal fluorescence microscope. In addition, through staining of colorectal tissue of a living mouse ingesting DSS with moxifloxacin, it can be observed that there is no light emission from cells due to collapse of the crypt or destruction of the goblet cells caused by DSS.

Experimental Example 4: Endoscopic Photographing of Moxifloxacin-Stained Colorectal Tissue of Living Mouse FIG. 7(a1), FIG. 7(a2), FIG. 7(b1), and FIG. 7(b2) are endoscopy images of moxifloxacin-stained colorectal tissue of a mouse, obtained by the fluorescence endoscopic method for visualization of colorectal tissue using fluoroquinolone antibiotics.

Figure 7:
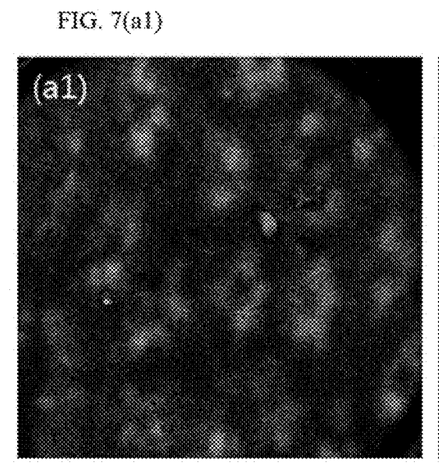

FIG. 7(a1) and FIG. 7(a2) are confocal endoscopic microscopy images of moxifloxacin-stained colorectal tissue of a normal mouse. Referring to FIG. 7(a1) and FIG. 7(a2), goblet cells of the colorectal tissue stained with moxifloxacin were fluorescence-excited and emitted light, whereby not only the number and shape of goblet cells but also the shape of the crypt could be observed.

FIG. 7(b1) and FIG. 7(b2) are confocal endoscopic microscopy images of moxifloxacin-stained colorectal tissue of a mouse ingesting DDS. Referring to FIG. 7(b1) and FIG. 7(b2), it could be observed that, as the mouse ingesting DDS developed colitis, the crypt of the colon of the mouse collapsed and the goblet cells were destroyed and were not distinct.

Therefore, it was confirmed that, through staining of goblet cells of colorectal tissue of a living mouse with moxifloxacin, fluorescence endoscopic observation of the goblet cells is possible while photographing of the goblet cells is possible using a high-magnification fluorescence microscope instead of a high-performance microscope, such as a confocal fluorescence microscope.

In addition, through staining of colorectal tissue of a living mouse ingesting DSS with moxifloxacin, it can be observed that there is no light emission from cells due to collapse of the crypt or destruction of the goblet cells caused by DSS.

Next, a method for diagnosis of lesions of colorectal tissue according to the present invention will be described.

In the method for diagnosis of lesions of colorectal tissue according to the present invention, lesions of the colorectal tissue are diagnosed using an image of goblet cells of the colorectal tissue, obtained by the fluorescence endoscopic method for visualization of colorectal tissue according to the present invention.

Diagnosis of the lesions of the colorectal tissue is conducted based on the number of goblet cells per unit area.

The goblet cells act as a lubricant and prevent intrusion of bacteria into the crypt by secreting mucus onto a surface of the crypt of the colon. Thus, the goblet cells play important roles in maintaining normal function of the crypt, and, upon development of lesions, there is a change in the number of goblet cells in the crypt.

For example, among intestinal bowel diseases (IBDs), in the case of ulcerative colitis (UC), the number of goblet cells decreases, and, in the case of Crohn's disease (CD), the number of goblet cells increases. Accordingly, these two lesions can be distinguished from each other using an image of the goblet cells of the colorectal tissue obtained by the fluorescence endoscopic method for visualization of colorectal tissue using fluoroquinolone antibiotics according to the present invention.

In addition, as to diagnosis of colorectal cancer, upon development of hyperplasia, there is no change in the number of goblet cells, whereas, upon development of adenoma, the number of goblet cells decreases, whereby these two lesions can be distinguished from each other.

Although some embodiments have been described herein, it should be understood that these embodiments are provided for illustration only and are not to be construed in any way as limiting the present invention, and that various modifications, changes, alterations, and equivalent embodiments can be made by those skilled in the art without departing from the spirit and scope of the invention.

What is claimed is:

1. A fluorescence endoscopic method for visualization of colorectal tissue using a fluoroquinolone antibiotic, comprising:
   staining goblet cells of a crypt of colorectal tissue of a colon and/or a rectum with a fluoroquinolone antibiotic;
   inserting an endoscope into the colon and/or the rectum, wherein the endoscope comprises a light source, and wherein the endoscope is a general fluorescence endoscope or a confocal endoscopic microscope;
   irradiating the colorectal tissue with single-photon excitation light from the light source of the endoscope for single-photon excitation of the fluoroquinolone antibiotic thereby inducing a fluorescence emission of the fluoroquinolone antibiotic corresponding to the single-photon excitation, wherein the single-photon excitation light has a wavelength band within a range from near ultraviolet (UV) light to visible light; and
   photographing the colorectal tissue including the fluorescence emission of the fluoroquinolone antibiotic using the endoscope thereby generating an image of the colorectal tissue including the goblet cells and the fluorescence emission.

2. The fluorescence endoscopic method according to claim 1, wherein the fluoroquinolone antibiotic comprises moxifloxacin.

3. The fluorescence endoscopic method according to claim 2, further comprising:
   determining a change in a number of goblet cells per unit area of the colorectal tissue using the image of the colorectal tissue including the goblet cells and the fluorescence emission; and
   diagnosing lesions of the colorectal tissue based on the change in the number of the goblet cells per unit area.

4. The fluorescence endoscopic method according to claim 3, wherein the lesions of the colorectal tissue comprise ulcerative colitis, Crohn's disease, hyperplasia, and adenoma.

5. The fluorescence endoscopic method according to claim 1, wherein the wavelength band is within a range from 300 nm to 476 nm.

6. The fluorescence endoscopic method according to claim 5, further comprising:
   determining a change in a number of goblet cells per unit area of the colorectal tissue using the image of the colorectal tissue including the goblet cells and the fluorescence emission; and
   diagnosing lesions of the colorectal tissue based on the change in the number of the goblet cells per unit area.

7. The fluorescence endoscopic method according to claim 6, wherein the lesions of the colorectal tissue comprise ulcerative colitis, Crohn's disease, hyperplasia, and adenoma.

8. The fluorescence endoscopic method according to claim 1, further comprising:

determining a change in a number of goblet cells per unit area of the colorectal tissue using the image of the colorectal tissue including the goblet cells the fluorescence emission; and     diagnosing lesions of the colorectal tissue based on the change in the number of the goblet cells per unit area.

9. The fluorescence endoscopic method according to claim 8, wherein the lesions of the colorectal tissue comprise ulcerative colitis, Crohn's disease, hyperplasia, and adenoma.

\* \* \* \* \*